United States Patent
Flanagan et al.

(10) Patent No.: US 8,267,081 B2
(45) Date of Patent: Sep. 18, 2012

(54) INHALED ANESTHETIC AGENT THERAPY AND DELIVERY SYSTEM

(75) Inventors: Craig T. Flanagan, New York City, NY (US); William S. Hurst, Burlington, WI (US); Lien-Lung Sheu, Berkley Heights, NJ (US); Thomas A. Block, Lake Bluff, IL (US); Haiming Wu, North Attleboro, MA (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 725 days.

(21) Appl. No.: 12/389,802

(22) Filed: Feb. 20, 2009

(65) Prior Publication Data
US 2010/0212668 A1 Aug. 26, 2010

(51) Int. Cl.
*A61M 15/00* (2006.01)
(52) U.S. Cl. ......... 128/203.16; 128/203.12; 128/204.18; 128/205.12
(58) Field of Classification Search ............. 128/200.24, 128/205.11, 205.27, 205.28, 203.16, 203.12, 128/204.18, 205.12
See application file for complete search history.

(56) References Cited

U.S. PATENT DOCUMENTS

| | | | |
|---|---|---|---|
| 575,714 A | 1/1897 | Heinzerling | |
| 999,950 A | 8/1911 | Berthelot | |
| 1,040,886 A | 10/1912 | Claude | |
| 1,082,482 A | 12/1913 | Tetee | |
| 1,312,117 A | 8/1919 | Hinkle | |
| 2,104,988 A | 1/1938 | Heidbrink | 128/203.28 |
| 2,837,413 A | 6/1958 | Hay | 422/49 |
| 3,088,810 A * | 5/1963 | Hay | 422/117 |
| 3,123,071 A | 3/1964 | Felts | 128/203.12 |
| 3,251,361 A | 5/1966 | Rusz | 128/188 |
| 3,301,255 A | 1/1967 | Thompson | 128/200.18 |
| 3,313,298 A | 4/1967 | Schreiber | 128/204.14 |
| 3,420,232 A | 1/1969 | Bickford | 128/203.25 |
| 3,465,753 A | 9/1969 | Levy et al. | 128/203.14 |
| 3,489,144 A | 1/1970 | Dibelius et al. | 128/205.12 |

(Continued)

FOREIGN PATENT DOCUMENTS

DE 41 05 228 A1 8/1992

(Continued)

OTHER PUBLICATIONS

International Search Report and Written Opinion from corresponding International Application No. PCT/US10/23551 (dated May 6, 2010).

*Primary Examiner* — Lynne Anderson
*Assistant Examiner* — Aundria Hairell
(74) *Attorney, Agent, or Firm* — Marshall, Gerstein & Borun LLP

(57) ABSTRACT

A therapy utilizing inhaled anesthetic agents (such as desflurane, sevoflurane, isoflurane, or xenon) for the sedation of patients outside of the immediate perioperative space such as in the medical intensive care unit (MICU) and the surgical intensive care unit (SICU). The therapy includes controlled delivery of volatile anesthetic agents to patients undergoing ventilatory support on an ICU ventilator over extended periods of time. A system which provides for the delivery of anesthetic agents includes an anesthetic agent vaporizer element, an anesthetic agent reflector, and a plug-in cassette which contains both a cartridge housing liquid phase volatile anesthetic agent and an anesthetic vapor scrubbing medium.

13 Claims, 5 Drawing Sheets

U.S. PATENT DOCUMENTS

| | | | | |
|---|---|---|---|---|
| 3,528,418 A | 9/1970 | Grosholz | | 128/200.13 |
| 3,534,732 A | 10/1970 | Bickford | | 128/203.14 |
| 3,536,430 A | 10/1970 | Kurihara | | 100/4 |
| 3,575,168 A | 4/1971 | Jones et al. | | 128/203.14 |
| 3,588,057 A | 6/1971 | Breiling | | 261/39.1 |
| 3,592,191 A | 7/1971 | Jackson | | 128/203.28 |
| 3,593,710 A | 7/1971 | Eichelman et al. | | 128/200.11 |
| 3,630,438 A | 12/1971 | Bickford | | 236/53 |
| 3,651,805 A | 3/1972 | Breiling | | 128/203.25 |
| 3,703,172 A | 11/1972 | Hay | | 128/200.13 |
| 3,820,959 A | 6/1974 | Wise et al. | | 422/211 |
| 3,836,129 A | 9/1974 | Perelmutr et al. | | 261/47 |
| 3,841,560 A | 10/1974 | Sielaff | | 239/136 |
| 3,842,833 A | 10/1974 | Ogle | | 128/200.18 |
| 3,851,645 A | 12/1974 | Connel | | 128/203.25 |
| 3,873,806 A | 3/1975 | Schossow | | 392/402 |
| 3,940,064 A | 2/1976 | Takaoka | | 239/74 |
| 3,941,573 A | 3/1976 | Chapel | | 96/135 |
| 4,015,599 A | 4/1977 | Peterson | | 128/204.13 |
| 4,017,566 A | 4/1977 | Seidel | | 261/56 |
| 4,058,120 A | 11/1977 | Caparrelli et al. | | 128/203.12 |
| 4,059,657 A | 11/1977 | Hay | | 261/104 |
| 4,067,935 A | 1/1978 | Jones et al. | | 128/203.14 |
| 4,091,056 A | 5/1978 | Hamalainen et al. | | 261/19 |
| 4,094,317 A | 6/1978 | Wasnich | | 128/200.16 |
| 4,106,503 A | 8/1978 | Rosenthal et al. | | 128/200.18 |
| 4,112,939 A | 9/1978 | Visconti | | 128/203.25 |
| 4,129,621 A | 12/1978 | Jones et al. | | 261/39.1 |
| 4,150,670 A | 4/1979 | Jewett et al. | | 128/204.22 |
| 4,253,453 A | 3/1981 | Hay | | 128/200.19 |
| 4,303,601 A | 12/1981 | Grimm et al. | | 261/142 |
| 4,350,662 A | 9/1982 | Dowgul et al. | | 422/122 |
| 4,353,366 A | 10/1982 | Bickford | | 128/205.12 |
| 4,434,790 A | 3/1984 | Olesen | | 128/200.14 |
| 4,444,182 A | 4/1984 | Gregory | | 128/204.14 |
| 4,471,773 A | 9/1984 | Bunnell et al. | | 128/204.21 |
| 4,477,395 A | 10/1984 | Albarda | | 261/131 |
| 4,484,576 A | 11/1984 | Albarda | | 128/202.22 |
| 4,491,459 A | 1/1985 | Pinkerton | | 96/113 |
| 4,497,701 A | 2/1985 | Murata et al. | | 204/430 |
| 4,508,117 A | 4/1985 | Rodari | | 128/204.21 |
| 4,527,558 A | 7/1985 | Hoenig | | 128/205.24 |
| 4,552,141 A | 11/1985 | Torri | | 128/205.12 |
| 4,571,543 A | 2/1986 | Raymond et al. | | 324/425 |
| 4,576,159 A | 3/1986 | Hahn et al. | | 128/203.14 |
| 4,587,966 A | 5/1986 | Albarda | | 128/202.22 |
| 4,607,634 A | 8/1986 | Clapham | | 128/203.25 |
| 4,611,590 A | 9/1986 | Ryschka et al. | | 128/203.14 |
| 4,681,099 A | 7/1987 | Sato et al. | | 128/204.23 |
| 4,691,700 A | 9/1987 | Brychta et al. | | 128/200.21 |
| 4,693,853 A | 9/1987 | Falb et al. | | 261/39.1 |
| 4,708,831 A | 11/1987 | Elsworth et al. | | 261/130 |
| 4,747,402 A | 5/1988 | Reese et al. | | 128/204.21 |
| 4,750,483 A | 6/1988 | Ankartross et al. | | 128/203.26 |
| 4,770,168 A | 9/1988 | Rusz et al. | | 128/203.12 |
| 4,791,922 A | 12/1988 | Lindsay-Scott et al. | | 128/205.28 |
| 4,798,689 A | 1/1989 | Heim et al. | | 261/39.1 |
| 4,805,609 A | 2/1989 | Roberts et al. | | 128/200.21 |
| 4,823,784 A | 4/1989 | Bordoni et al. | | 128/200.14 |
| 4,879,997 A | 11/1989 | Bickford | | 128/200.21 |
| 4,881,541 A | 11/1989 | Eger, II et al. | | 128/203.25 |
| 4,890,479 A * | 1/1990 | Glover et al. | | 73/23.31 |
| 4,905,685 A | 3/1990 | Olsson et al. | | 128/203.12 |
| 4,919,125 A | 4/1990 | Heaton et al. | | 128/203.14 |
| 4,928,685 A | 5/1990 | Gray | | 128/204.24 |
| 4,932,398 A | 6/1990 | Lancaster et al. | | 128/200.14 |
| 4,982,734 A | 1/1991 | Green et al. | | 128/200.14 |
| 5,033,464 A | 7/1991 | Dlcastilho | | 128/205.19 |
| 5,036,842 A | 8/1991 | van der Smissen et al. | | 128/204.18 |
| 5,044,361 A | 9/1991 | Werner et al. | | 128/204.16 |
| 5,044,363 A | 9/1991 | Burkhart | | 128/205.27 |
| 5,062,999 A | 11/1991 | Wallroth et al. | | 261/39.1 |
| 5,063,922 A | 11/1991 | Hakkinen | | 128/200.16 |
| 5,072,726 A | 12/1991 | Mazloomdoost et al. | | 128/200.14 |
| 5,094,235 A | 3/1992 | Westenskow et al. | | 128/204.22 |
| 5,114,441 A | 5/1992 | Kanner et al. | | 95/98 |
| 5,119,807 A | 6/1992 | Roberts et al. | | 128/200.24 |
| 5,119,810 A | 6/1992 | Kiske et al. | | 128/204.26 |
| 5,146,915 A | 9/1992 | Montgomery | | 128/203.14 |
| 5,156,776 A | 10/1992 | Loedding et al. | | 261/27 |
| 5,168,866 A | 12/1992 | Montgomery | | 128/203.12 |
| 5,188,645 A | 2/1993 | Fukuhori et al. | | 95/113 |
| 5,197,462 A | 3/1993 | Falb et al. | | 128/203.14 |
| 5,207,220 A | 5/1993 | Long | | 128/207.14 |
| 5,207,640 A | 5/1993 | Hattler | | 604/28 |
| 5,231,980 A | 8/1993 | Filipovic et al. | | 128/205.12 |
| 5,235,971 A | 8/1993 | Falb et al. | | 128/203.14 |
| 5,237,990 A | 8/1993 | Psaros et al. | | 128/204.21 |
| 5,243,973 A | 9/1993 | Falb et al. | | 128/203.27 |
| 5,287,849 A | 2/1994 | Piper et al. | | 128/203.12 |
| 5,299,568 A | 4/1994 | Forare et al. | | 128/205.11 |
| 5,309,903 A | 5/1994 | Long | | 128/203.12 |
| 5,337,738 A | 8/1994 | Heinonen | | 128/203.12 |
| 5,368,021 A | 11/1994 | Beard et al. | | 128/205.12 |
| 5,372,172 A | 12/1994 | Iseki | | 152/548 |
| 5,381,836 A | 1/1995 | Braatz et al. | | 141/21 |
| 5,383,449 A | 1/1995 | Forare et al. | | 128/205.11 |
| 5,388,571 A | 2/1995 | Roberts et al. | | 128/203.12 |
| 5,390,665 A | 2/1995 | Leach | | 128/203.25 |
| 5,419,316 A | 5/1995 | Bernstein | | 128/203.12 |
| 5,443,059 A | 8/1995 | Koch et al. | | 128/200.16 |
| 5,456,247 A | 10/1995 | Shilling et al. | | 128/203.12 |
| 5,471,979 A | 12/1995 | Psaros et al. | | 128/205.28 |
| 5,478,506 A | 12/1995 | Lavimodiere | | 261/72.1 |
| 5,482,033 A | 1/1996 | Engle et al. | | 128/205.19 |
| 5,485,828 A | 1/1996 | Hauser | | 128/200.16 |
| 5,490,500 A | 2/1996 | Reichert et al. | | 128/204.13 |
| 5,492,111 A | 2/1996 | Tinker et al. | | 128/203.12 |
| 5,509,405 A | 4/1996 | Mashak | | 128/203.12 |
| 5,509,406 A | 4/1996 | Kock et al. | | 128/203.14 |
| 5,515,845 A | 5/1996 | Filipovic et al. | | 128/205.12 |
| 5,520,169 A | 5/1996 | Georgieff et al. | | 128/204.16 |
| 5,535,737 A | 7/1996 | Galbenu | | 128/203.14 |
| 5,537,992 A | 7/1996 | Bjoernstijerna et al. | | 128/203.14 |
| 5,546,931 A | 8/1996 | Rusz | | 128/203.12 |
| 5,568,910 A | 10/1996 | Koehler et al. | | 251/83 |
| 5,584,916 A | 12/1996 | Yamashita et al. | | 96/123 |
| 5,592,934 A | 1/1997 | Thwaites | | 128/203.12 |
| 5,603,314 A | 2/1997 | Bono | | 128/200.21 |
| 5,605,146 A | 2/1997 | Sarela | | 128/203.12 |
| 5,611,332 A | 3/1997 | Bono | | 128/200.18 |
| 5,615,669 A | 4/1997 | Olsson et al. | | 128/203.12 |
| 5,619,986 A | 4/1997 | Werner et al. | | 128/204.21 |
| 5,636,626 A | 6/1997 | Bloch et al. | | 128/203.12 |
| 5,645,052 A | 7/1997 | Kersey | | 128/203.26 |
| 5,649,531 A | 7/1997 | Heinonen | | 128/203.12 |
| 5,657,747 A | 8/1997 | Holliday | | 128/202.27 |
| 5,664,561 A | 9/1997 | Kersey | | 128/203.26 |
| 5,666,946 A | 9/1997 | Langenback | | 128/200.16 |
| 5,671,729 A | 9/1997 | Moll et al. | | 128/203.14 |
| 5,673,688 A | 10/1997 | Tham et al. | | 128/204.22 |
| 5,694,924 A | 12/1997 | Cewers | | 128/204.21 |
| 5,701,888 A | 12/1997 | Tham et al. | | 128/204.21 |
| 5,715,813 A | 2/1998 | Guevrekian | | 128/205.12 |
| 5,722,449 A | 3/1998 | Heinonen et al. | | 137/101.19 |
| 5,727,545 A | 3/1998 | Psaros | | 128/203.12 |
| 5,739,535 A | 4/1998 | Koch et al. | | 250/339.13 |
| 5,752,502 A | 5/1998 | King | | 128/200.18 |
| 5,769,071 A | 6/1998 | Turnbull | | 128/203.12 |
| 5,769,072 A | 6/1998 | Olsson et al. | | 128/205.13 |
| 5,771,882 A | 6/1998 | Psaros et al. | | 128/203.12 |
| 5,778,872 A | 7/1998 | Fukunaga et al. | | 128/202.27 |
| 5,799,711 A | 9/1998 | Heinonen et al. | | 141/18 |
| 5,806,513 A | 9/1998 | Tham et al. | | 128/204.22 |
| 5,829,428 A | 11/1998 | Walters et al. | | 128/200.24 |
| 5,832,917 A | 11/1998 | Sarela et al. | | 128/203.12 |
| 5,845,633 A | 12/1998 | Psaros | | 128/200.24 |
| 5,871,564 A | 2/1999 | McCombs | | 95/98 |
| 5,918,593 A | 7/1999 | Loser | | 128/200.16 |
| 5,918,595 A | 7/1999 | Olsson et al. | | 128/203.26 |
| 5,921,235 A | 7/1999 | Kronekvist | | 128/203.12 |
| 5,924,419 A | 7/1999 | Kotliar | | 128/205.11 |
| 5,931,161 A | 8/1999 | Keilbach et al. | | 128/204.22 |
| 5,938,117 A | 8/1999 | Ivri | | 239/4 |

| Patent No. | Date | Inventors | Class |
|---|---|---|---|
| 5,957,129 A | 9/1999 | Tham et al. | 128/204.28 |
| 5,967,141 A | 10/1999 | Heinonen | 128/203.12 |
| 5,978,548 A | 11/1999 | Holmstrand et al. | 392/397 |
| 5,983,891 A | 11/1999 | Fukunaga | 128/200.24 |
| 5,983,896 A | 11/1999 | Fukunaga et al. | 128/207.14 |
| 6,021,777 A | 2/2000 | Post et al. | 128/204.13 |
| 6,029,660 A | 2/2000 | Calluaud et al. | 128/203.12 |
| 6,032,665 A | 3/2000 | Psaros | 128/203.12 |
| 6,041,777 A | 3/2000 | Faithfull et al. | 128/200.24 |
| 6,116,235 A | 9/2000 | Walters et al. | 128/200.24 |
| 6,125,847 A | 10/2000 | Lin | 128/204.17 |
| 6,134,914 A | 10/2000 | Eschwey et al. | 62/637 |
| 6,138,672 A | 10/2000 | Kankkunen | 128/203.12 |
| 6,152,133 A | 11/2000 | Psaros et al. | 128/205.12 |
| 6,155,255 A | 12/2000 | Lambert | 128/203.16 |
| 6,155,256 A | 12/2000 | Wallin | 128/203.16 |
| 6,206,002 B1 | 3/2001 | Lambert | 128/205.12 |
| 6,213,120 B1 | 4/2001 | Block et al. | 128/204.23 |
| 6,216,690 B1 | 4/2001 | Keitel et al. | 128/203.12 |
| 6,220,242 B1 | 4/2001 | Wallin | 128/203.12 |
| 6,230,666 B1 | 5/2001 | Wallin et al. | 122/406.3 |
| 6,253,767 B1 | 7/2001 | Mantz | 128/205.13 |
| 6,263,874 B1 | 7/2001 | LeDez et al. | 128/206.21 |
| 6,275,650 B1 | 8/2001 | Lambert | 392/395 |
| 6,279,576 B1 | 8/2001 | Lambert | 128/205.28 |
| 6,286,505 B1 | 9/2001 | Psaros | 128/203.12 |
| 6,289,891 B1 | 9/2001 | Cewers | 128/203.12 |
| 6,294,000 B1 | 9/2001 | Klobucar | 95/113 |
| 6,296,002 B1 | 10/2001 | Tashchyan | 135/96 |
| 6,298,845 B1 | 10/2001 | Hoglund et al. | 128/203.12 |
| 6,302,104 B1 | 10/2001 | Kronekvist | 128/203.12 |
| 6,348,083 B1 | 2/2002 | Chevalier et al. | 95/47 |
| 6,390,987 B1 | 5/2002 | Graham | 600/529 |
| 6,394,084 B1 | 5/2002 | Nitta | 128/201.13 |
| 6,394,087 B1 | 5/2002 | Kankkunen et al. | 128/203.16 |
| 6,405,539 B1 | 6/2002 | Stach et al. | 62/3.4 |
| 6,443,150 B1 | 9/2002 | Pessala et al. | 128/203.14 |
| 6,474,335 B1 | 11/2002 | Lammers | 128/205.12 |
| 6,488,028 B1 | 12/2002 | Lambert | 128/205.12 |
| 6,521,026 B1 | 2/2003 | Goto | 96/122 |
| 6,530,370 B1 | 3/2003 | Heinonen | 128/200.16 |
| 6,539,937 B1 | 4/2003 | Haveri | 128/200.21 |
| 6,540,153 B1 | 4/2003 | Ivri | 239/4 |
| 6,547,853 B2 | 4/2003 | Fukuhori et al. | 95/113 |
| 6,557,551 B2 | 5/2003 | Nitta | 128/203.17 |
| 6,558,451 B2 | 5/2003 | McCombs et al. | 95/98 |
| 6,564,799 B2 | 5/2003 | Fukunaga et al. | 128/205.29 |
| 6,581,600 B2 | 6/2003 | Bird | 128/203.24 |
| 6,585,016 B1 * | 7/2003 | Falligant et al. | 141/352 |
| 6,591,836 B1 | 7/2003 | Fuhrman et al. | 128/205.24 |
| 6,598,602 B1 | 7/2003 | Sjoholm | 128/200.16 |
| 6,606,989 B1 | 8/2003 | Brand et al. | 128/200.16 |
| 6,620,107 B2 | 9/2003 | Payne et al. | 600/532 |
| 6,629,646 B1 | 10/2003 | Ivri | 239/4 |
| 6,631,717 B1 | 10/2003 | Rich et al. | 128/205.13 |
| 6,634,355 B2 | 10/2003 | Colas | 128/203.12 |
| 6,662,802 B2 | 12/2003 | Smith et al. | 128/203.16 |
| 6,672,306 B2 | 1/2004 | Loser et al. | 128/203.12 |
| 6,681,998 B2 | 1/2004 | Sharpe et al. | 239/13 |
| 6,691,702 B2 | 2/2004 | Appel et al. | 128/202.26 |
| 6,705,316 B2 | 3/2004 | Blythe et al. | 128/204.18 |
| 6,712,770 B2 | 3/2004 | Lin et al. | 600/532 |
| 6,729,329 B2 | 5/2004 | Berry | 128/204.16 |
| 6,745,771 B2 | 6/2004 | Castor et al. | 128/205.27 |
| 6,745,800 B1 * | 6/2004 | Sansom | 141/198 |
| 6,764,534 B2 | 7/2004 | McCombs et al. | 96/111 |
| 6,767,391 B2 | 7/2004 | Tanaka et al. | 96/115 |
| 6,837,244 B2 | 1/2005 | Yagi et al. | 128/205.11 |
| 6,863,067 B2 | 3/2005 | Loncar | 128/203.12 |
| 6,874,500 B2 | 4/2005 | Fukunaga et al. | 128/204.18 |
| 6,877,510 B2 | 4/2005 | Nitta | 128/203.17 |
| 6,894,359 B2 | 5/2005 | Bradley et al. | 257/414 |
| 6,929,007 B2 | 8/2005 | Emerson | 128/205.12 |
| 6,949,133 B2 | 9/2005 | McCombs et al. | 96/111 |
| 6,951,216 B2 | 10/2005 | Heinonen | 128/203.25 |
| 6,962,153 B2 | 11/2005 | Gershteyn | 128/203.12 |
| 6,981,947 B2 | 1/2006 | Melker | 600/532 |
| 6,988,497 B2 | 1/2006 | Levine | 128/203.27 |
| 6,990,977 B1 | 1/2006 | Calluaud et al. | 128/203.12 |
| 7,007,693 B2 | 3/2006 | Fuhrman et al. | 128/205.12 |
| 7,011,092 B2 | 3/2006 | McCombs et al. | 128/205.12 |
| 7,014,634 B2 | 3/2006 | Hodgson | 604/512 |
| 7,017,575 B2 | 3/2006 | Yagi et al. | 128/205.11 |
| 7,032,595 B2 | 4/2006 | Bunke et al. | 128/203.25 |
| 7,052,468 B2 | 5/2006 | Melker et al. | 600/532 |
| 7,066,029 B2 | 6/2006 | Beavis et al. | 73/649 |
| 7,066,913 B2 | 6/2006 | Kullik et al. | 604/246 |
| 7,069,928 B1 | 7/2006 | Waldo, Jr. et al. | 128/201.13 |
| 7,073,500 B2 | 7/2006 | Kates | 128/203.16 |
| 7,077,133 B2 | 7/2006 | Yagi et al. | 128/204.26 |
| 7,077,134 B2 | 7/2006 | Ahlmen | 128/205.12 |
| 7,077,136 B2 | 7/2006 | Ahlmen et al. | 128/205.27 |
| 7,146,977 B2 | 12/2006 | Beavis et al. | 128/203.12 |
| 7,207,123 B2 | 4/2007 | Tanahashi et al. | 34/80 |
| 7,235,222 B2 | 6/2007 | Hotta et al. | 423/235 |
| 7,246,621 B2 | 7/2007 | McNeirney | 128/205.12 |
| 7,250,035 B1 | 7/2007 | Ott et al. | 604/26 |
| 7,305,984 B2 | 12/2007 | Altobelli et al. | 128/200.14 |
| 7,306,657 B2 | 12/2007 | Yagi et al. | 96/121 |
| 7,353,825 B2 | 4/2008 | Orr et al. | 128/205.12 |
| 7,481,215 B2 | 1/2009 | Rossen et al. | 128/203.12 |
| 7,490,607 B2 * | 2/2009 | Bottom et al. | 128/203.12 |
| 7,522,040 B2 | 4/2009 | Passmore et al. | 340/540 |
| 7,547,931 B2 | 6/2009 | Star et al. | 257/253 |
| 7,596,965 B2 | 10/2009 | Berry et al. | 62/532 |
| 7,628,034 B2 | 12/2009 | Berry et al. | 62/617 |
| 7,644,594 B2 | 1/2010 | Berry et al. | 62/617 |
| 7,669,438 B2 | 3/2010 | Berry et al. | 62/617 |
| 7,704,214 B2 | 4/2010 | Abraham-Fuchs et al. | 600/532 |
| 2001/0022181 A1 | 9/2001 | Masson et al. | 128/203.12 |
| 2002/0069876 A1 | 6/2002 | Loser et al. | 128/203.19 |
| 2002/0088461 A1 | 7/2002 | Alksnis | 128/203.13 |
| 2002/0117471 A1 | 8/2002 | Colas | 128/203.12 |
| 2003/0079745 A1 | 5/2003 | Bunke et al. | 128/203.12 |
| 2003/0103338 A1 | 6/2003 | Vandentop et al. | 361/767 |
| 2003/0140922 A1 | 7/2003 | Dunlop | 128/203.12 |
| 2003/0233086 A1 | 12/2003 | Burns, Jr. et al. | 604/512 |
| 2004/0084048 A1 | 5/2004 | Stenzler et al. | 128/206.12 |
| 2004/0089297 A1 | 5/2004 | Videbrink | 128/203.12 |
| 2004/0099267 A1 | 5/2004 | Ahlmen et al. | 128/203.12 |
| 2004/0194781 A1 | 10/2004 | Fukunaga et al. | 128/203.12 |
| 2004/0216743 A1 | 11/2004 | Orr et al. | 128/205.12 |
| 2005/0039747 A1 | 2/2005 | Fukunaga et al. | 128/204.18 |
| 2005/0072420 A1 | 4/2005 | Gershteyn | 128/200.19 |
| 2005/0129573 A1 | 6/2005 | Gabriel et al. | 422/58 |
| 2005/0133030 A1 | 6/2005 | Fiedorowicz | 128/204.13 |
| 2005/0155380 A1 | 7/2005 | Rock | 62/617 |
| 2005/0188990 A1 | 9/2005 | Fukunaga et al. | 128/204.18 |
| 2005/0235831 A1 | 10/2005 | Taveira et al. | 96/111 |
| 2005/0247316 A1 | 11/2005 | Orr | 128/205.12 |
| 2005/0257790 A1 | 11/2005 | McNeirney | 128/203.12 |
| 2005/0263154 A1 | 12/2005 | Baker et al. | 128/204.22 |
| 2005/0279987 A1 | 12/2005 | Star et al. | 257/9 |
| 2006/0065269 A1 | 3/2006 | Gippert et al. | 128/203.12 |
| 2006/0090750 A1 | 5/2006 | Rossen et al. | 128/200.14 |
| 2006/0102181 A1 | 5/2006 | McCombs et al. | 128/204.26 |
| 2006/0201503 A1 | 9/2006 | Breen | 128/204.18 |
| 2006/0207593 A1 | 9/2006 | Dittmann et al. | 128/203.12 |
| 2006/0225735 A1 | 10/2006 | Bottom et al. | 128/203.12 |
| 2006/0254587 A1 | 11/2006 | Berry et al. | 128/204.16 |
| 2006/0254589 A1 | 11/2006 | Berry et al. | 128/205.12 |
| 2006/0254590 A1 | 11/2006 | Berry et al. | 128/205.12 |
| 2006/0263255 A1 | 11/2006 | Han et al. | 422/83 |
| 2006/0266357 A1 | 11/2006 | McCombs et al. | 128/204.26 |
| 2007/0048180 A1 | 3/2007 | Gabriel et al. | 422/57 |
| 2007/0048181 A1 | 3/2007 | Chang et al. | 422/57 |
| 2007/0071651 A1 | 3/2007 | Kato et al. | 422/83 |
| 2007/0079827 A1 | 4/2007 | Lambert | 128/200.14 |
| 2007/0125376 A1 | 6/2007 | Reinstadtler | 128/203.26 |
| 2007/0132043 A1 | 6/2007 | Bradley et al. | 257/414 |
| 2007/0208243 A1 | 9/2007 | Gabriel et al. | 600/347 |
| 2007/0295328 A1 | 12/2007 | Raghuprasad | 128/200.21 |
| 2008/0021339 A1 | 1/2008 | Gabriel et al. | 600/532 |
| 2008/0035148 A1 | 2/2008 | Fuhrman et al. | 128/205.15 |
| 2008/0060641 A1 | 3/2008 | Smith et al. | 128/200.16 |
| 2008/0066749 A1 | 3/2008 | Reichert et al. | 128/203.12 |
| 2008/0093226 A1 | 4/2008 | Briman et al. | 205/775 |
| 2008/0105258 A1 | 5/2008 | Deane et al. | 128/204.21 |

| | | | | | | |
|---|---|---|---|---|---|---|
| 2008/0221806 A1 | 9/2008 | Bryant et al. ................ 702/22 | DE | 10106010 | | 7/2002 |
| 2008/0236577 A1 | 10/2008 | Power et al. ............ 128/203.12 | EP | 0 338 518 | A2 | 10/1989 |
| 2008/0262370 A1 | 10/2008 | Varney et al. ................ 600/532 | EP | 0 339 828 | B1 | 11/1989 |
| 2008/0295826 A1 | 12/2008 | Altobelli et al. ........ 128/200.14 | EP | 0 348 019 | B1 | 12/1989 |
| 2009/0078254 A1 | 3/2009 | Rock ........................ 128/204.16 | EP | 0 338 518 | A3 | 8/1990 |
| 2009/0095288 A1 | 4/2009 | Haveri ..................... 128/200.14 | EP | 0 338 518 | B1 | 6/1993 |
| 2009/0095295 A1 | 4/2009 | Wruck et al. ............ 128/203.26 | EP | JP 6-86818 | | 3/1994 |
| 2009/0095296 A1 | 4/2009 | Wruck et al. ............ 128/203.27 | EP | 0 566 488 | B1 | 9/1996 |
| 2009/0241948 A1 | 10/2009 | Clancy et al. ............ 128/203.14 | GB | 300444 | | 11/1928 |
| 2009/0261845 A1 | 10/2009 | Hierlemann et al. ......... 324/658 | GB | 2 029 572 | A | 3/1980 |
| 2009/0277448 A1 | 11/2009 | Ahlmen et al. .......... 128/204.21 | GB | 2254005 | | 9/1992 |
| 2009/0288659 A1 | 11/2009 | Haveri et al. ............ 128/203.14 | WO | WO 88/07876 | | 10/1988 |
| 2010/0024816 A1 | 2/2010 | Weinstein et al. ....... 128/203.27 | WO | WO 92/05826 | | 4/1992 |
| 2010/0043794 A1 | 2/2010 | Saito et al. ............... 128/204.22 | WO | WO 99/40961 | | 8/1999 |
| 2010/0071698 A1 | 3/2010 | Kiritake .................. 128/205.27 | WO | WO 01/07108 | | 2/2001 |
| 2010/0074881 A1 | 3/2010 | Boucher et al. ............... 424/94.6 | WO | WO 03/090826 | | 11/2003 |
| 2010/0078027 A1 | 4/2010 | Ogasahara ............... 128/205.12 | WO | WO 2004/060459 | A1 | 7/2004 |
| 2010/0085067 A1 | 4/2010 | Gabriel et al. ................ 324/663 | WO | WO 2004/087244 | A1 | 10/2004 |
| 2010/0108063 A1 | 5/2010 | Koch et al. ............... 128/204.15 | WO | WO 2006/009498 | A1 | 1/2006 |
| | | | WO | WO/2006/124578 | A2 | 11/2006 |
| | FOREIGN PATENT DOCUMENTS | | WO | WO 2008/017566 | A1 | 2/2008 |
| DE | 41 05 971 A1 | 8/1992 | * cited by examiner | | | |
| DE | 10039557 | 2/2002 | | | | |

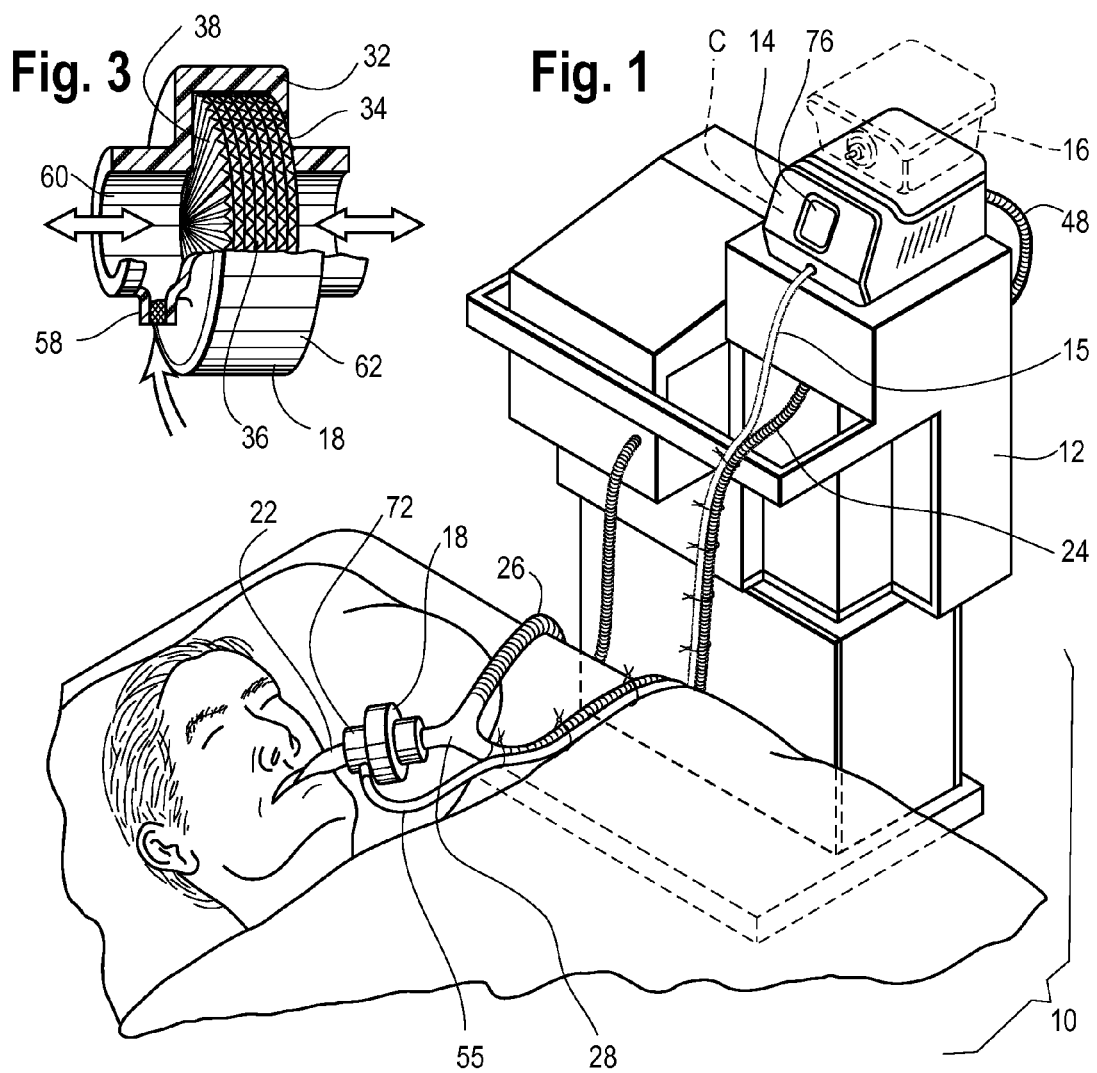

INHALED ANESTHETIC AGENT THERAPY AND DELIVERY SYSTEM

BACKGROUND

1. Field of the Disclosure

This disclosure relates generally to devices for administering anesthesia to patients and, more particularly, to the long term delivery of inhaled anesthetic agents to intubated patients undergoing ventilatory support outside of the perioperative environment; and devices for the delivery of said agents.

2. Description of the Related Art

Anesthesia using volatile anesthetic agents is commonplace. The properties of inhaled anesthetics are well known in the literature for their favorable properties, including rapid onset and recovery, controllability and a favorable safety profile. Such favorable properties more closely approximate an 'ideal' agent than common intravenously-delivered (IV) agents typically used in the intensive care unit (ICU) environment for patient sedation. To the present day, the use of volatile anesthetic agents has been (largely) limited to operating rooms (OR's) for procedures where the clinical objectives include rendering and maintaining unconsciousness, analgesia and amnesia.

A therapy of the present disclosure involves the use of these agents outside of the OR. Specifically, this disclosure includes a therapy in which the above clinical objectives are carried out outside the perioperative environment; such as in the ICU. The therapy of the present disclosure involves the use of primarily sub-maximum allowable concentration (sub-MAC) dosages of these agents over periods which can extend to multiple days in contrast to OR-based use of these agents in which patients are typically sedated at higher MAC concentrations and for shorter periods of time (hours). Additionally, the optimal volatile anesthetic agent for the therapy is described, and one embodiment of a hardware configuration suitable for implementation of this therapy is described in detail.

The origins of inhaled anesthetic agents can be traced back to the late $18^{th}$ century when British clergyman, philosopher, and educator, Joseph Priestly, first identified the gas nitrous oxide. Priestly's prodigy, Humphrey Davy, later recognized the analgesic effects of nitrous oxide in the early $19^{th}$ century. Early attempts at using anesthetic agents for pain-free surgery included the use of Diethyl Ether, Chloroform, and Nitrous Oxide and the origins of the practice of anesthesiology is typically traced to the 1840's when the first operation using such agents for the excision of a neck mass was performed at Massachusetts General Hospital by Dr. William Morton (although others claim to have used the agents earlier). The somewhat concurrent rise of the use of injectable local anesthetics traces back to the 1850's when morphine was first injected for treatment of painful neuralgias. The use of other injectable and IV agents followed including cocaine in the 1880's, and procaine in the early 1900's. The science of both inhaled and IV anesthetic compounds has, of course, progressed and today common inhaled agents include sevoflurane, isoflurane, and desflurane. Common IV anesthetics have progressed from chloral hydrate, to short acting barbiturates such as thiopental, to the common medications used today such as propofol, midazolam and dexmedatomidine.

To this day, the use of inhaled agents is generally limited to the operating room (OR), (although uses in MRI and Labor and Delivery settings are envisioned), and patients who have undergone surgical procedures are typically switched from inhaled agents in the OR to IV medications when moved (post-surgery) to the intensive care unit (ICU). All IV medications currently in use for sedation suffer from drawbacks including undesirable variability in patient wakeup time following discontinuation, and difficulty in clinical control of depth of sedation. Modern inhaled anesthetics such as desflurane, by contrast, are widely regarded as having rapid onset and recovery, and good controllability. Therefore, it is the intent of the therapy and system of this disclosure to extend the useful range of inhaled anesthetics beyond the operating room environment into the ICU environment for intubated, mechanically ventilated patient populations. Further, it is the intent of the present disclosure to extend the duration of therapy from hours, as is current practice in the OR, to potentially (multiple) days of therapy.

In order to achieve these goals, a hardware system will be described which integrates into existing technologies being used in the ICU environment for patient respiratory support. Specifically, the therapy of the present disclosure integrates with typical ICU ventilators, and as such provides inhaled agents to the patient concomitant with ventilator gas flow. The integration of the technology is not ventilator specific, meaning that it will integrate with any modern ICU ventilator. Further the technology is not mode specific and will work independent of ventilator mode and settings, ensuring broad functionality of the technology with modern ICU ventilators.

Prior art can be broadly classified as falling into three categories, first are patents related to technologies for anesthetic vapor delivery in an OR setting, second are patents on volatile anesthetic scavenging/reclamation as applied to the OR setting, and third are patents related to anesthetic reflector technologies for the on-airway conservation of anesthetic vapor for use outside the OR setting.

It is an object of the present disclosure to provide an anesthesia therapy and device which can be implemented using modern, microprocessor-based ICU ventilators. This objective being, in general, at odds with the plurality of art which seeks to provide such therapy in an OR setting. The difference in clinical setting may require different sedative regimens, as well as technology with notably different pneumatic and functional characteristics.

BRIEF DESCRIPTION OF THE DRAWINGS

FIG. 1 is a perspective view of the vaporizer-based anesthesia delivery system of the present disclosure;

FIG. 2 is a partially exploded perspective view of a package containing a refill cassette and a reflector for use in the vaporizer-based anesthesia delivery system of FIG. 1;

FIG. 3 is a perspective view of a reflector, partially broken away, for use as part of the vaporizer-based anesthesia delivery system of FIG. 1;

SUMMARY OF DISCLOSURE

The Therapy

Figure 4:
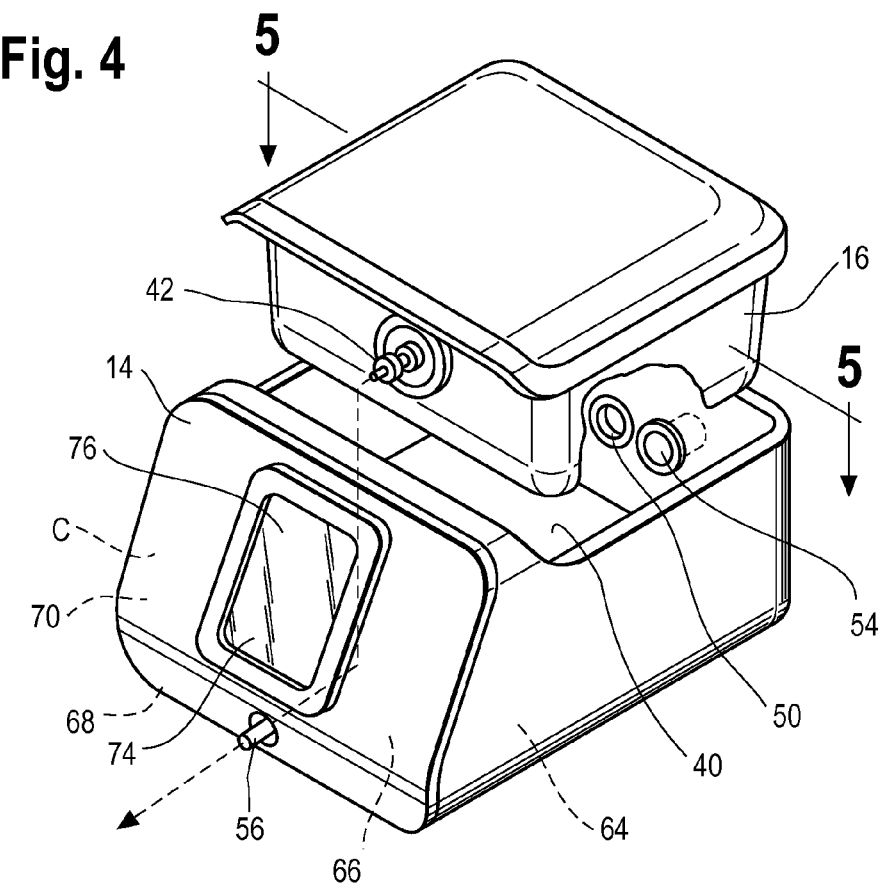
FIG. 4 is an exploded perspective view of a vaporizer and refill cassette of the anesthesia delivery system of FIG. 1.
Figure 5:
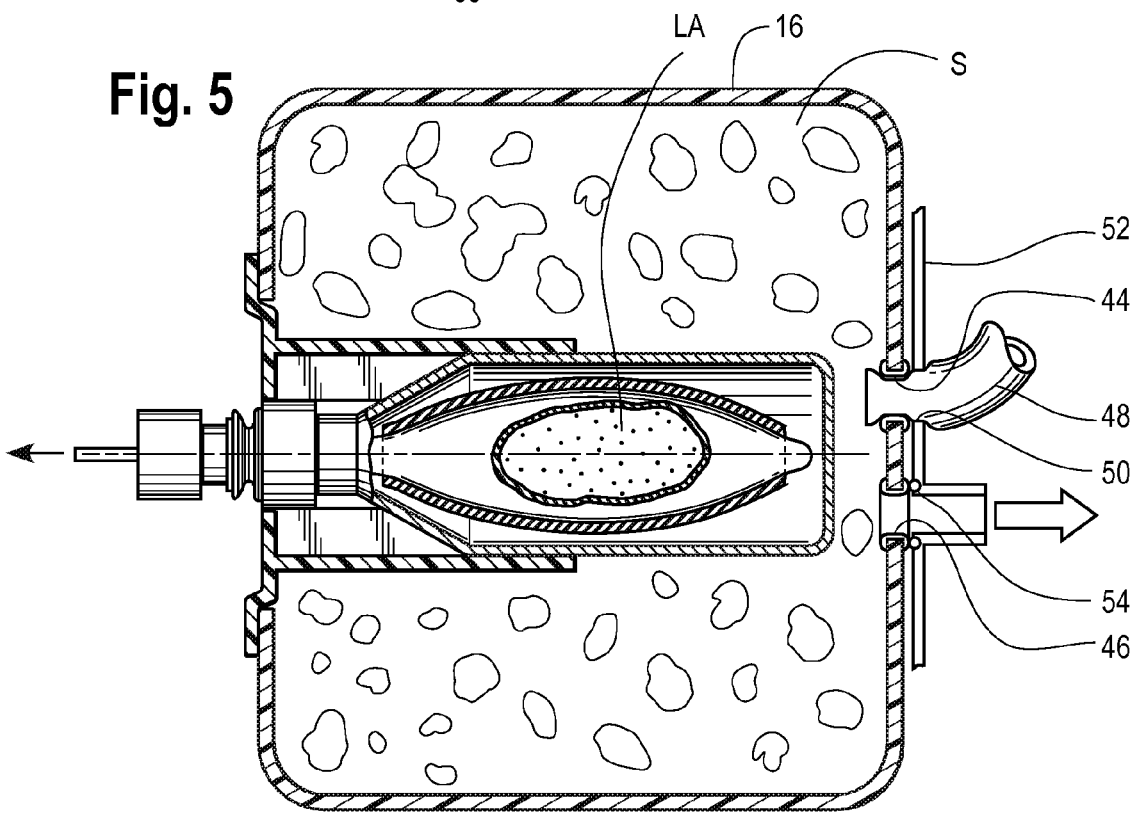
FIG. 5 is a cross-sectional view of the refill cassette of the anesthesia delivery system of FIG. 1, taken along lines 5-5 of FIG. 4, the refill cartridge containing a bottle of an anesthetic agent to be vaporized and a surrounding scrubbing agent for filtering exhaled gases.

The therapy of the present disclosure involves the delivery of volatile anesthetic agent (preferably using, but not limited to, desflurane) for patients undergoing mechanical ventilatory support using an ICU ventilator, in an ICU or similar setting. The therapy generally includes sub-MAC dosages of the anesthetic agents over short to prolonged periods of up to several days. The use of such agents, which will decrease or replace the use of sedative IV medications in these patients, is intended to provide therapeutic benefit and/or cost advantages over IV medications commonly in use in the ICU.

Therapeutic benefits may include a reduction in ICU and hospital length of stay (LOS), an increased predictability and reduction in patient wake-up time, a reduction of incidents of self-extubation, and a reduction in morbidity and mortality.

The therapy includes the delivery of physician controlled desflurane vapor to the breathing circuit of patients undergoing ventilatory support. The physician will select the end tidal concentration of the agent to be delivered, this concentration being reflective of patient alveolar (deep lung) concentration. It is intended that the patients' end tidal concentration will be held at this clinician selected level until intervention such as a concentration settings change or until patient extubation is performed by a clinician.

The therapy of the present disclosure may be applied to the use of all modern volatile anesthetic agents including isoflurane, sevoflurane and desflurane. Isoflurane, the least expensive agent of the three and a reasonable candidate for use with the invention described here, might be obviated by its high blood and tissue solubility The use of isoflurane (an older agent) in the OR environment was associated with a longer wake-up time and return to cognitive function compared to newer agents such as desflurane. Sevoflurane, also a reasonable candidate for use with the therapy of the present disclosure, can produce a buildup of inorganic fluorides in the body of patients ostensibly due to metabolism of the agent. While the buildup of these fluorides has not been proven clinically to be dangerous in such patients, the levels seen after multiple day usage of this agent are worrisome to clinicians and, as a result, sevoflurane is a less attractive agent for this invention. Sevoflurane fat and muscle solubility coefficients are as high as isoflurane and this may lead to prolonged elimination. Finally, desflurane is the lowest soluble agent in blood, fat and muscle; also desflurane presents the lowest degree of biodegradation (0.02% compared to isoflurane 0.2% and sevoflurane 5%). In summary, desflurane does not possess the attendant drawbacks noted for isoflurane and sevoflurane and is, thus, currently seen as the agent of choice for the therapy of the present disclosure with two caveats. The first caveat being that since desflurane boils at room temperature due to its high vapor pressure, it presents unique technical challenges relative to its controlled delivery in a clinical environment. The second caveat being that desflurane has not (as of the writing of this patent) been proven to be free of the buildup of dangerous metabolites or the production of significant side-effects when used on a multi-day basis.

DETAILED DESCRIPTION OF THE PREFERRED EMBODIMENTS

In order to integrate with a typical ICU ventilator, the hardware platform must provide many of the functions of a modern anesthesia workstation including a method for the controlled delivery of volatile anesthetic vapor to the patient airway, a method for clearing of exhaled carbon dioxide ($CO_2$), a method of producing adequate airway humidification, and a method of sequestering of exhaust anesthetic vapor to prevent pollution of the clinical environment. In addition, in order to be compatible with modern ICU ventilators, the therapy must be relatively pneumatically transparent to the ventilator. Pneumatic transparency implies that the therapy will not introduce a large amount of compressible volume to the patient circuit (in order to prevent lowered effective ventilation i.e. subsequent reductions in the volume of fresh gas entering the patients lungs). Further, the therapy must not introduce significant additional resistance to gas flow in the patient circuit as flow resistance can produce trapping of end exhalation lung gas leading to inadvertent positive end expiratory pressure (inadvertent PEEP). In the preferred embodiment of the present disclosure, the ICU ventilator functions as it normally would, providing fresh gas flow from the inspiratory circuit, and exhausting exhaled, $CO_2$ laden gas to the exhaust port and is not functionally impaired or compromised by the presence of the additional components of the system.

FIG. 1 shows the hardware system 10 for the preferred embodiment at a systems level. The hardware system 10 is intended to be functional with a modern ICU ventilator 12 and is also intended to function to hold end tidal anesthetic agent concentrations at the set level regardless of ventilator setting or mode. The hardware configuration includes three primary elements: a vapor delivery device, also referred to herein as a vaporizer 14, a disposable or reusable anesthetic cassette 16, and an anesthetic reflector 18.

The vapor delivery device 14 serves the purpose of vaporizing liquid phase volatile anesthetic agents and delivering these agents, in vapor phase, and in a controlled fashion, to the patient airway.

The disposable or reusable anesthetic cassette 16 includes two primary elements, a cartridge 20 containing liquid phase volatile anesthetic agent LA and a scrubber agent S responsible for removing waste anesthetic gas from the exhausted breathing path.

Finally, the anesthetic reflector 18 is a device which is placed between the patient endotracheal tube 22 and a connector joining an inspiratory limb 24 and an expiratory limb 26 of a two-limb patient circuit to the endotracheal tube 22, referred to herein as a patient circuit WYE 28 and functions to conserve the volume of anesthetic required for therapy thereby reducing the drug consumption and monetary cost of the therapy.

The concentration of the anesthetic agent, such as desflurane, will be monitored and controlled by the system of the present disclosure using an anesthetic agent sensor AAS internal to the vaporizer element 14 and this sampled concentration will be used by a closed loop controller C (also internal to the vaporizer 14 and in electronic communication with the anesthetic agent sensor AAS) to maintain the anesthetic agent concentration at the clinician selected level.

As shown in FIG. 2, the disposables for the hardware system 10, including the anesthetic reflector 18 and the cartridge 20, may be supplied in a disposable or reusable package 30 to clinicians based on therapy duration (e.g. the contents of one package 30 provides 8 hours of therapy).

The Reflector

The reflector 18 shown in FIG. 3 includes a (preferably transparent) plastic, tubular outer shell 32, which is dimensionally constructed to interface with both the endotracheal tube 22 and the patient circuit WYE 28 by press fit. The reflector 18 houses an adsorbent media 34. Adsorbents are high surface area materials (1000 m$^2$/g) that collect vapors out of an enriched gas stream and have been observed to subsequently release vapors into a lean gas stream. In addition, the reflector 18 optionally includes at least one filter medium 36 to prevent the free movement of adsorbent media 34 into the patient airway. The reflector also optionally includes heat and moisture exchanger (HME) media 38 for preservation of patient airway humidification. Such HME media is typically hygroscopic or hydrophobic in nature. The reflector 18 preferably has an enlarged-diameter central portion 62 in which the adsorbent media 34, the filter media 36, and the HME media 38 are provided.

The reflector 18 is designed to have a relatively low airflow resistance (approximately 1-2 cmH$_2$O drop at 60 LPM flow) and relatively low internal volume (<100 ml) so as to ensure adequate fresh gas ventilation of the patient ensuring that the re-breathing of CO$_2$-laden gas is minimized. The reflector 18 is designed with specific adsorbent material(s) which work well with desflurane (i.e. produce good capture and release efficiencies and kinetics). Finally, the reflector 18 is designed to be effective for at least the therapeutic lifespan of the anesthetic cassette 16 and is designed to be relatively low cost in construction as it is a disposable element of the therapy.

The Cassette

The cassette 16 is a disposable and/or reusable element of the system 10 designed both to provide volatile anesthetic agent in liquid form to the vaporizer element and to scrub exhausted breathing gas of anesthetic agent. In order to achieve this functionality, the anesthetic agent cartridge 20 (described in more detail below) and aggressive scrubber media are co-located and pneumatically isolated from one another in the same anesthetic cassette 16. FIG. 4 shows the basic configuration of the cassette 16, which is designed to easily drop into a cavity 40 in the vaporizer 14 and removably plug into the vaporizer 14 for rapid change out once the cassette 16 is depleted. The cassette 16 is designed such that the anesthetic agent LA and the scrubber S have an equivalent therapeutic lifespan ensuring that both elements are somewhat equally consumed at the end of the cartridge therapeutic life of the cartridge 20.

The anesthetic agent LA is volatile, and is housed in an aerosol or pressurized cartridge 20 which is capped by a valve 42 which is normally sealed and opens when engaged with a receiving mechanism located in the vaporizer 14. The scrubber agent S is packed around the cartridge 20. The cassette 16 is provided with an exhausted ventilator gas inlet port 44 and a vent outlet port 46.

Exhaled gas is drawn from the patient, through the endotracheal tube 22, through the reflector 18 (with at least some of the exhaled anesthesia agent being caught by the adsorbent 34 within the reflector 18), through the patient circuit WYE 28 and the expiratory limb 26 of the patient circuit, and to the ventilator 12. An exhausted ventilator gas tube 48 feeds exhausted air from the ventilator 12 to the exhausted ventilator gas inlet port 44. A gas-tight inlet aperture 50 may be provided in wall 52 of the cavity 40 of the vaporizer 14 to facilitate connection between the exhausted ventilator gas tube 48 and the exhausted gas inlet port 44. Exhausted ventilator gas circulates through the cassette 16 and past the scrubber agent S, before being vented through the vent outlet port 46. At least one vent outlet aperture 54 may also be provided in wall 52 of the cavity 40 of the vaporizer 14, so that scrubbed gas may be vented from the vent outlet port 46 to the surrounding atmosphere in the clinical environment. As the anesthetic agent has been scrubbed from the gas prior to venting, medical professionals and other patients in the clinical environment will not be exposed to unacceptable levels of anesthetic vapor in the air.

Since this system 10 is intended for use in an ICU (and possibly OR) clinical environment, and further since the system 10 is designed to (preferably) impose little if any additional workload on the clinicians over existing technologies, such as IV delivery of medicaments, the cassette 16 itself is thus designed to be rapidly changed out (of the overall system) with little effort and time required of the clinicians. This can be achieved by self locking (electronic or mechanical) or user latched mechanisms which engage the cassette 16 with the vaporizer 14 in a liquid and air tight coupling.

The cassette 16 in one embodiment may be electronically identified as being a valid (non-counterfeit) cassette 16 by the use of an RFID tag affixed to the cassette which is in turn read by the vaporizer system during cassette engagement (plug-in). Using such an RFID (or similar electromagnetic or optical identification) modality, only valid cassettes would be allowed by the system 10 for use in therapy and counterfeit cassettes 16 would generate a system halt. This measure being taken to prevent the use of counterfeit cassettes 16 with the system and further to ensure that only approved volatile anesthetic agent can be used for the therapy.

The Vaporizer

The vaporizer 14 contains internal hardware which takes liquid phase anesthetic agent LA from the cassette 16, converts it to vapor phase anesthetic agent, and delivers it, in controlled fashion, to the patient airway through a tube 55 that leads from a vaporized anesthetic outlet port 56 on the vaporizer 14 to a vaporized anesthetic inlet port 58 provided on a side of the reflector 18 opposite the patient circuit WYE. As shown in FIG. 3, the vaporized anesthetic inlet port 58 may be provided on the outer shell 32 of the reflector between an endotracheal tube interface connection 60 of the reflector 18 (by which the reflector 18 connects to the endotracheal tube 22) and an enlarged-diameter central portion 62 of the reflector containing the adsorbent 34, the filter medium 36 and the HME media 38.

Figure 8:
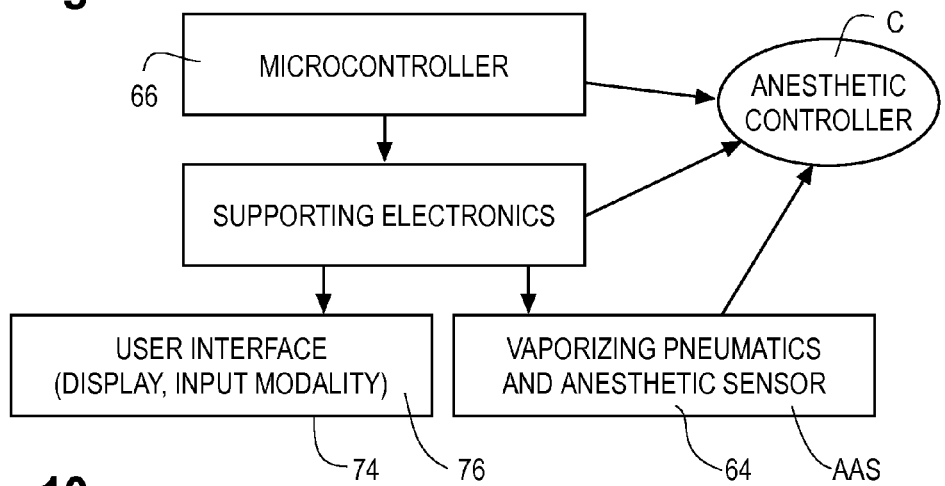
FIG. 8 is a schematic diagram of the components of the vaporizer of the anesthesia delivery system of FIG. 1.

The internal elements of the vaporizer 14 are represented schematically in FIG. 8 and include a vaporizing technology 64, a microcontroller 66 and supporting electronics, a pump 68, pressure and/or flow sensors 70, and at least one volatile anesthetic sensor element 72. Suitable vaporizing technology 64 may include, but is not limited to, the use of wicks for evaporative production of anesthetic vapor, the use of heated sumps with bypass gas flow which entrains anesthetic vapor, and the use of valves to precisely deliver liquid anesthetic to a gas stream wherein it is vaporized. The vaporizer 14 draws gas out of the patient airway (distal to the endotracheal tube 22 and proximal to the reflector 18) and records the airway concentration using the anesthetic sensor element 72. The gas is then preferably returned through a multi-lumen umbilical to the patient airway. The concentration of anesthetic agent, as measured by the anesthetic sensor element 72, is then used as the feedback signal for a closed loop feedback system, including the microcontroller 66, which is employed to hold the end tidal level of anesthetic agent at a clinician-selected level. Closed loop anesthetic agent delivery is realized by a controlled flow of vapor phase agent out of the vaporizer 14 through the multi-lumen umbilical and into the patient circuit.

The vaporizer microcontroller 66 provides control for the entire system and as such, monitors and controls system function and can provide user alarm functionality. The vaporizer 14 is preferably provided with a user interface 74, including a display 76 and an input modality 78, such as a touch-sensitive screen or push buttons.

The Cartridge

The cartridge 20 of the cassette 16 may include a pressurize-able metallic or plastic housing similar to an aerosol paint can in which the internal volatile anesthetic agent is pressurized by a gas propellant and liquid anesthetic agent is allowed to exit via a spring activated valve. The internal anesthetic agent may be separated from the gas propellant by a flexible medium which maintains hermetic isolation between the agent and the propellant. It is further understood that the pressurized propellant may serve to prevent such high vapor pressure agents as desflurane from boiling (inasmuch as desflurane at atmospheric pressure boils at room temperature).

Figure 6:
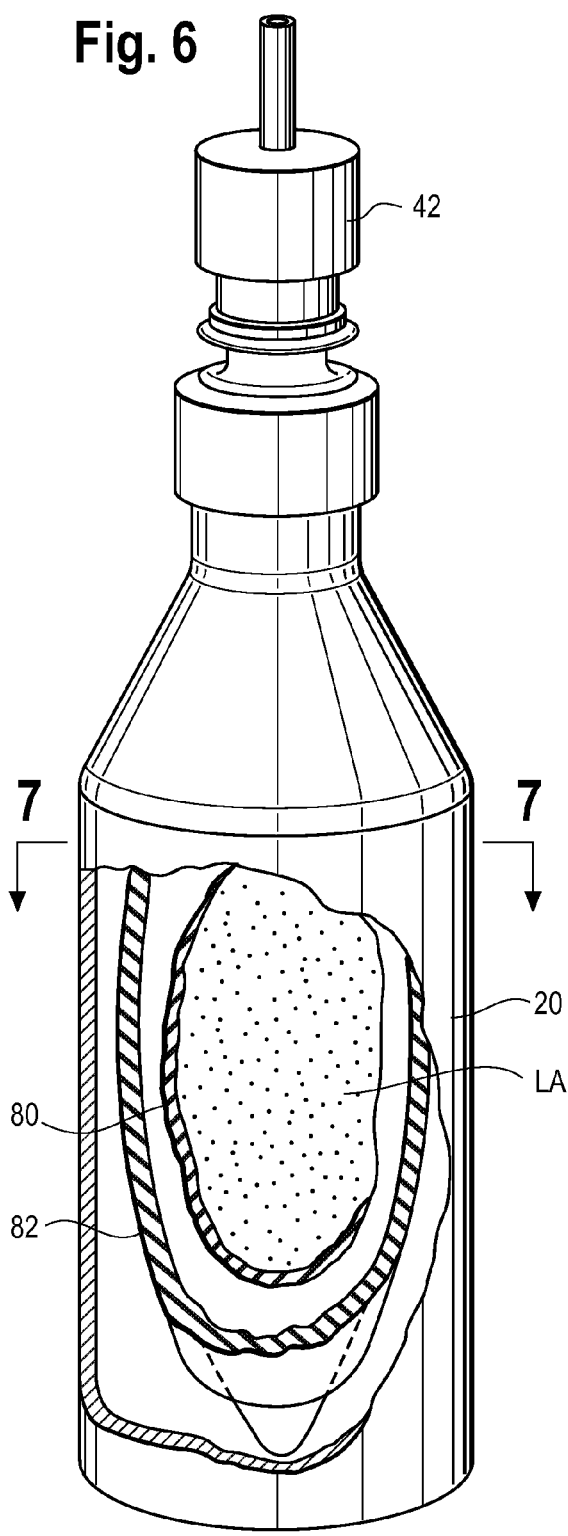
FIG. 6 is a perspective view, partially broken away, of the bottle of anesthetic agent provided in the refill cassette.
Figure 7:
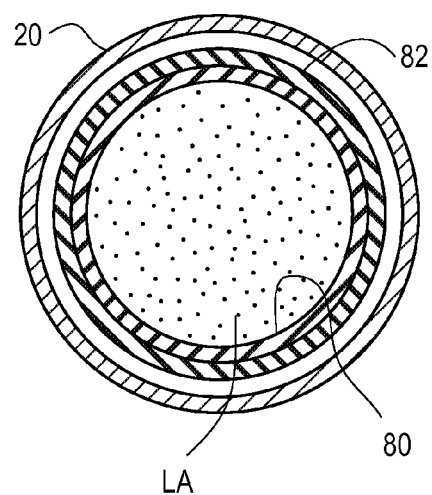
FIG. 7 is a cross-sectional view of the bottle of anesthetic agent, taken along lines 7-7 of FIG. 6.

An alternate embodiment of the cartridge 20 is shown in FIGS. 6 and 7, in which a rubber banding places consistent pressure on an internal bladder 80 which houses liquid volatile anesthetic agent LA thus allowing for nearly consistent anesthetic liquid outlet pressure during use of the cartridge 20. The bladder 80 may use an external rubber tube 82 surrounding the bladder 80 to exert pressure onto the bladder walls forcing the liquid anesthetic agent LA out of the bladder 80. In order to ensure that the anesthetic agent LA inside the cartridge can be used without ambient agent leakage, the interface between the cartridge 20 and the vaporizer 14 must be sealed.

Anesthetic Scrubbing Media

The anesthetic scrubbing media S may include an absorbent and/or adsorbent and/or chemically reactive media which is co-located with, yet hermetically isolated from the internal contents of the cartridge 20. The scrubbing media S and cassette 20 being designed to allow exhaled gas to pass through the scrubbing media S facilitating the scrubbing of the anesthetic agent from this waste exhaled gas. It is further understood that the scrubbing media S might be disposable or might consist of materials such as zeolites (e.g., silacalite—a hydrophobic zeolite which has been shown to capture volatile anesthetic agents effectively) which may allow for the reuse of both the zeolite material as well as the recycling of the captured anesthetic agent after a post-processing stage.

The anesthetic scrubbing agent is either in pelletized form or is sufficiently loosely packed so as not to significantly increase resistance to exhaled gas flow.

Additional embodiments of this anesthetic scrubbing element S incorporate the use of active elements which scrub or capture the anesthetic given the input of external energy to the process. Such elements might include a miniature condenser based on (for instance) liquid oxygen or liquid nitrogen cooled devices oriented to cool the gas stream allowing for condensation of the anesthetic vapor into a collection reservoir for either external pharmaceutical post-processing for eventual reuse or for immediate reintroduction to the patient airway. A further embodiment of this anesthetic scrubbing element incorporates the use of pressure based devices such as miniature compressors which seek to condense out the anesthetic vapor by pressurizing the exhalation gas stream.

Alternate Embodiment

Figure 9:
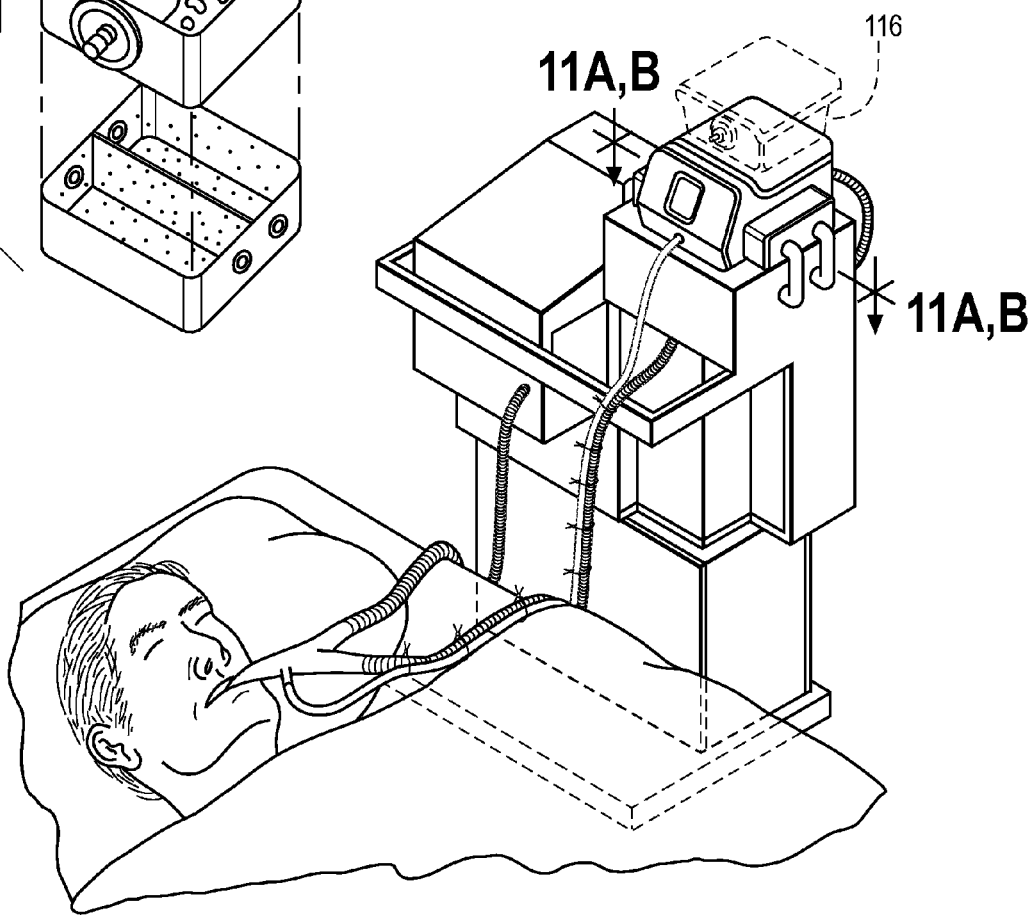
FIG. 9 is a perspective view of an alternate embodiment of the vaporizer-based anesthetic delivery system of the present disclosure.

An alternate preferred embodiment of the present disclosure shares many of the elements of the preferred embodiment, however, notably absent from this embodiment is the reflector element. Further, the construct of the plug-in cassette is somewhat different with another stage being added to this element. FIG. 9 shows the alternate preferred embodiment from a systems level and as seen during therapy. This alternate preferred embodiment has four patient circuits which plug into the vaporizer body. These patient circuits include the inhale and exhale circuits of the ventilator, and two circuits which extend from the vaporizer body to the patient. In addition, there continues to exist an exhaust scrubbing line which plugs into the back of the cassette as in the first preferred embodiment, described above. However as described below, this exhaust scrubbing capability is optional. Finally, as with the first preferred embodiment, this alternate preferred embodiment is highly pneumatically transparent to the ventilator, thus imposing little additional resistance to gas flow and only a small amount of additional compressible volume to the patient circuit.

The Cassette

Figure 10:
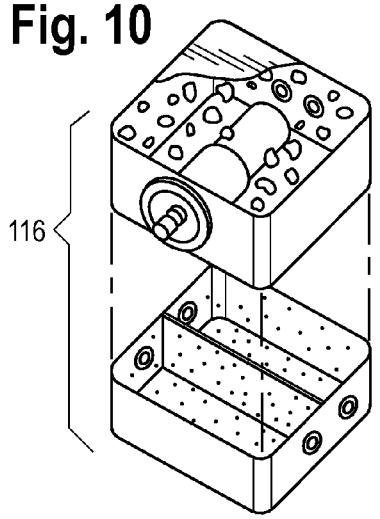
FIG. 10 is a schematic diagram of a cassette of the alternate embodiment of the vaporizer-based anesthetic delivery system of FIG. 9.
Figure 11A:
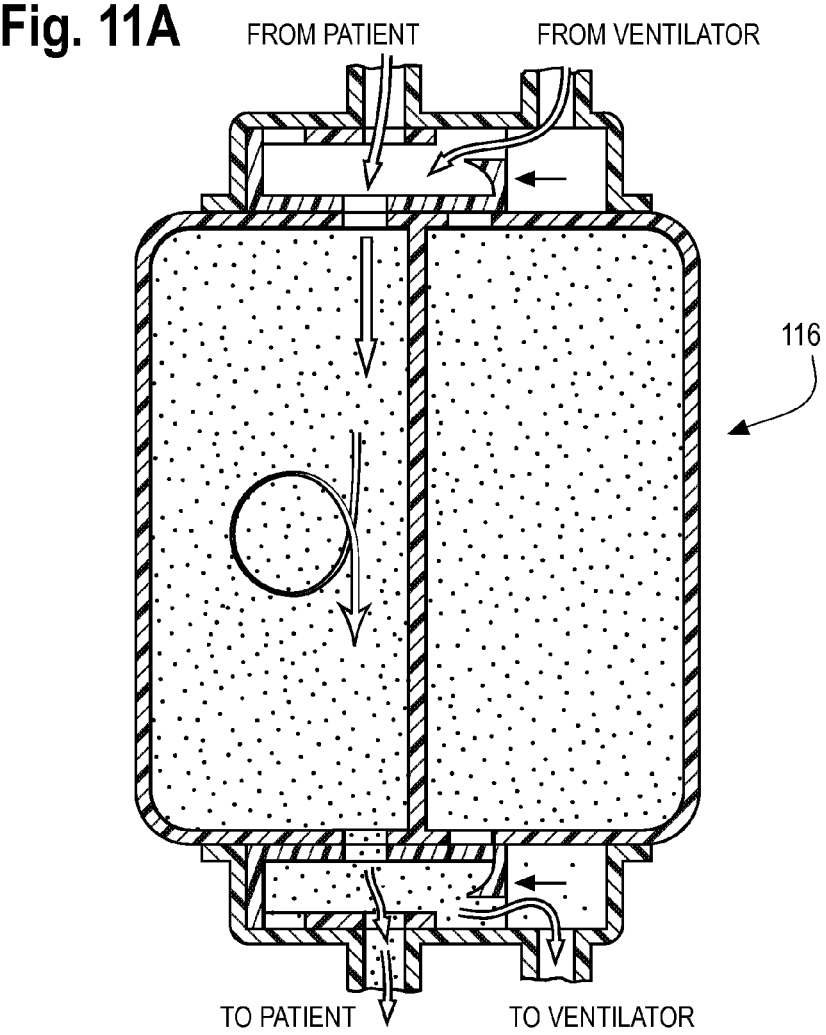
FIG. 11 is a schematic view of a lower portion of the cassette of FIG. 10, with FIG. 11a illustrating a gas flow path through the lower portion of the cassette in a first state, and FIG. 11b illustrating a gas flow path through lower portion of the cassette in a second state.
Figure 11B:
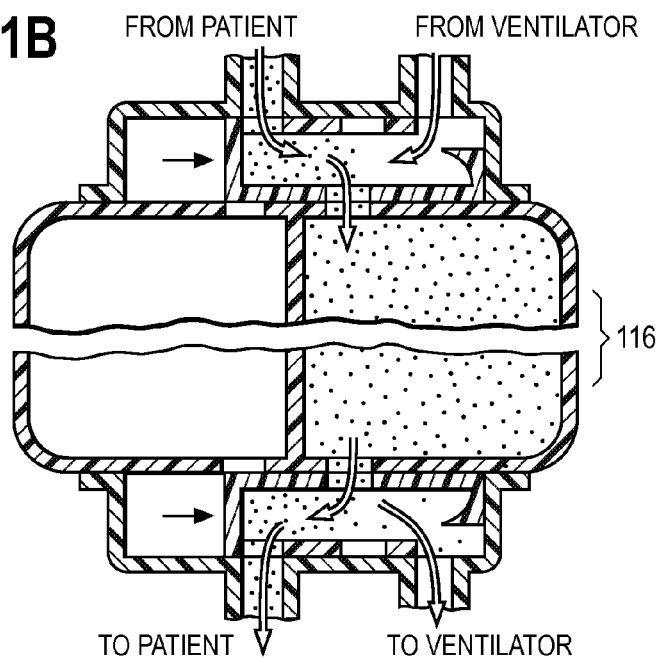

The cassette 116 (as illustrated in FIGS. 10 and 11) of the alternate preferred embodiment includes an upper level and a lower level, designed for distinct functional roles. The upper level of the cassette is intended to perform the same functions as the cassette 16 described in the first embodiment, described above, and serves to both supply volatile anesthetic agent to the vaporizer, as well as to scrub ventilator exhaust gas of residual volatile anesthetic agent before releasing exhaust gas into the clinical environment. The lower level of the cassette includes two pneumatically isolated adsorbent beds which, when the cassette 116 is connected to the vaporizer, allows for the switching of gas flow between the two.

For example, during a period of ventilation the gas flow paths will be configured with the inhale path traversing one of the two adsorbent beds, while the exhale path traverses the other. During this period, exhaled volatile anesthetic agent will accumulate in the adsorbent bed of the exhaled gas path resulting from exhaled gas laden with anesthetic agent. At some point, "Breakthrough" of anesthetic agent will occur in this exhaled gas path. Breakthrough is defined as a sudden and significant increase in volatile anesthetic agent being evident at the adsorbent bed on the ventilator side of the exhaled path. When breakthrough is sensed (preferably by an anesthetic sensor located within the body of the vaporizer element) the adsorbent material on the exhaled path is assumed to be functionally saturated with anesthetic agent. Therefore, at this time the vaporizer will switch internal valve states placing the two adsorbent beds in the others' former pneumatic path. This switching allows the now saturated adsorbent bed which was previously in the exhale path, to be placed in the inhale path. When this occurs, adsorbed anesthetic agent will be available for release from this saturated adsorbent bed into the inhaled gas stream of the patient. This process the repeats itself during the course of therapy, always utilizing breakthrough as a trigger to switch pneumatic paths.

Such a pneumatic implementation will lead to relatively high efficiencies of agent conservation, as the noted pneumatic pathway changes always occur when exhausted agent levels are first noted to be rising significantly from a low baseline level. This configuration might also obviate the need for the scrubber element located in the upper portion of the cassette given that the technique provides acceptably low agent release into the clinical environment.

The Vaporizer

The vaporizer in the second preferred embodiment performs the same functions as the vaporizer described in the first preferred embodiment, with two notable differences. First the vaporizer now includes valves (and optionally manifolds) allowing for the switching of the pneumatic pathways between the two adsorbent beds as described earlier. Second, an anesthetic sensor to sense anesthetic breakthrough is additionally preferably provided.

While various embodiments have been described herein, it is understood that the appended claims are not intended to be limited thereto, and may include variations that are still within the literal or equivalent scope of the claims.

We claim:

1. An anesthetic delivery system for use with a ventilator in communication with a patient circuit WYE and an endotracheal tube, the anesthetic delivery system comprising:
   a vaporizer having a cavity therein, the vaporizer including a vaporized anesthesia outlet;
   a removable cassette received in the cavity of the vaporizer, the cassette having an interior including a supply of an anesthetic agent and a scrubbing material;
   a tube having a first end in communication with the vaporized anesthesia outlet of the vaporizer and a second end configured to be placed in communication with the endotracheal tube, wherein the cassette includes an exhausted ventilator gas inlet through which expelled gas is delivered to the interior of the cassette.

2. The anesthetic delivery system of claim 1, wherein the cassette further includes a scrubbed gas outlet through which exhausted ventilator gas that is first filtered through the scrubbing material is vented to an exterior of the cassette.

3. The anesthetic delivery system of claim 2, wherein the vaporizer includes an inlet port in communication with the exhausted ventilator gas inlet of the cassette and a vent opening in communication with the scrubbed gas outlet.

4. An anesthetic delivery system for use with a ventilator in communication with a patient circuit WYE and an endotracheal tube, the anesthetic delivery system comprising:
   a vaporizer having a cavity therein, the vaporizer including a vaporized anesthesia outlet;
   a removable cassette received in the cavity of the vaporizer, the cassette having an interior including a supply of an anesthetic agent and a scrubbing material;
   a tube having a first end in communication with the vaporized anesthesia outlet of the vaporizer and a second end configured to be placed in communication with the endotracheal tube, wherein the removable cassette includes an upper level and a lower level, and the upper level supplies volatile anesthetic agent to the vaporizer and scrubs ventilator exhaust gas of residual volatile anesthetic agent before releasing exhaust gas into the environment.

5. An anesthetic delivery system for use with a ventilator in communication with a patient circuit WYE and an endotracheal tube, the anesthetic delivery system comprising:
   a vaporizer having a cavity therein, the vaporizer including a vaporized anesthesia outlet;
   a removable cassette received in the cavity of the vaporizer, the cassette having an interior including a supply of an anesthetic agent and a scrubbing material;
   a tube having a first end in communication with the vaporized anesthesia outlet of the vaporizer and a second end configured to be placed in communication with the endotracheal tube, wherein the removable cassette includes an upper level and a lower level, and the lower level includes two adsorbent beds, which, when the removable cassette is connected to the vaporizer, allow for a switching of gas flow between the two adsorbent beds.

6. The anesthetic delivery system of claim 5, further including an inhale path that traverses one of the two adsorbent beds of the cassette, and an exhale path that traverses the other of the two adsorbent beds of the cassette.

7. The anesthetic delivery system of claim 6, wherein exhaled volatile anesthetic agent accumulates in the adsorbent bed of the exhale path until a breakthrough occurs in the exhale path.

8. The anesthetic delivery system of claim 7, wherein the vaporizer switches internal valve states when the breakthrough occurs, placing the two adsorbent beds in the other's former pneumatic path, such that a saturated adsorbent bed of the exhale path is in the inhale path and available for release into the inhale path.

9. The anesthetic delivery system of claim 6, wherein the vaporizer repeatedly switches internal valve states each time one of the two adsorbent beds is saturated during delivery of anesthetic agent and a breakthrough occurs in one of the exhale path or the inhale path.

10. The anesthetic delivery system of claim 1, further comprising a reflector disposed between the patient circuit WYE and the second end of the tube, the reflector including a housing and an adsorbent material disposed within the housing.

11. The anesthetic delivery system of claim 10, wherein the reflector further comprises at least one filter medium disposed between the adsorbent material and a port of the reflector in communication with the second end of the tube.

12. The anesthetic delivery system of claim 10, wherein the reflector further includes at least one heat and moisture exchanger medium.

13. The anesthetic delivery system of claim 1, wherein the vaporizer includes an anesthetic agent sensor in electronic communication with a closed loop controller for regulating a concentration of the anesthetic agent delivered from the vaporizer.

* * * * *